(12) United States Patent
Goyal et al.

(10) Patent No.: US 10,642,952 B2
(45) Date of Patent: *May 5, 2020

(54) SENSOR BASED MONITORING (71) Applicant: INTERNATIONAL BUSINESS MACHINES CORPORATION, Armonk, NY (US)

(72) Inventors: Munish Goyal, Yorktown Heights, NY (US); Kimberly Greene Starks, Nashville, TN (US); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/835,744

(22) Filed: Dec. 8, 2017

(65) Prior Publication Data
US 2018/0322240 A1 Nov. 8, 2018

Related U.S. Application Data

(63) Continuation of application No. 15/587,505, filed on May 5, 2017.

(51) Int. Cl.
*G16H 40/67* (2018.01)
*G06F 19/00* (2018.01)
(Continued)

(52) U.S. Cl.
CPC .......... *G06F 19/00* (2013.01); *G06F 19/3418* (2013.01); *G16H 40/63* (2018.01);
(Continued)

(58) Field of Classification Search
CPC ... G06F 19/3418; F24F 2120/10; F24F 11/30; G05B 2219/2614; G06Q 50/22; A61B 5/0022
(Continued)

(56) References Cited

U.S. PATENT DOCUMENTS 5,214,385 A * 5/1993 Gabriel ............ G01R 19/16542
320/121
6,968,294 B2 11/2005 Gutta et al.
(Continued)

FOREIGN PATENT DOCUMENTS

EP 2425771 3/2012

OTHER PUBLICATIONS

RDI Technologies; Safe Sleep Baby Monitor; http:/www.rdi-technologies.com/safesleepbabymonitor; retrieved from the Internet Dec. 9, 2016; 3 pages.
(Continued)

*Primary Examiner* — Rocio Del Mar Perez-Velez
*Assistant Examiner* — Alicia M. Choi
(74) *Attorney, Agent, or Firm* — Schmeiser, Olsen & Watts; Brian M. Restauro (57) ABSTRACT

A method for improving mobile sensor based monitoring is provided. The method includes continuously receiving in real time via sensors integrated within a wearable device of a user, vital sign data and movement based data associated with the user. Additionally, environmental data is continuously received via sensors located within a geographical area of the user. The vital sign data, movement based data, environmental data, and medical data are analyzed and current and future mental and physical conditions for the user are predicted. Recommended actions associated with modifying the current and future mental and physical conditions for the user are generated and presented. Current physical conditions for the user are monitored to determine if the recommended actions have been executed.

11 Claims, 5 Drawing Sheets

(51) Int. Cl.
| | | |
|---|---|---|
| *G16H 50/30* | (2018.01) | |
| *G16H 50/20* | (2018.01) | |
| *G16H 40/63* | (2018.01) | |
| *F24F 11/80* | (2018.01) | |
| *F24F 120/10* | (2018.01) | |
| *F24F 11/30* | (2018.01) | |

(52) U.S. Cl.
CPC ............ *G16H 40/67* (2018.01); *G16H 50/20* (2018.01); *G16H 50/30* (2018.01); *F24F 11/30* (2018.01); *F24F 11/80* (2018.01); *F24F 2120/10* (2018.01); *G05B 2219/2614* (2013.01)

(58) Field of Classification Search
USPC ........................................................ 700/275
See application file for complete search history.

(56) References Cited

U.S. PATENT DOCUMENTS

| | | | |
|---|---|---|---|
| 7,524,279 B2 | 4/2009 | Auphan | |
| 8,157,731 B2 * | 4/2012 | Teller ...................... | A61B 5/01 |
| 9,147,041 B2 | 9/2015 | Amarasingham et al. | |
| 9,223,935 B2 | 12/2015 | Heneghan et al. | |
| 9,292,008 B1 * | 3/2016 | Ahamed .................. | G06F 1/163 |
| 9,554,411 B1 * | 1/2017 | Hall ...................... | A61B 5/0026 |
| 10,110,046 B1 | 10/2018 | Esquibel | |
| 2006/0202816 A1 * | 9/2006 | Crump ................ | A61B 5/02055 |
| | | | 340/539.12 |
| 2011/0004110 A1 * | 1/2011 | Shusterman ............ | G06F 19/00 |
| | | | 600/509 |
| 2012/0071731 A1 * | 3/2012 | Gottesman ............ | A61B 5/6833 |
| | | | 600/301 |
| 2012/0290266 A1 * | 11/2012 | Jain ........................ | G16H 40/63 |
| | | | 702/187 |
| 2013/0063550 A1 * | 3/2013 | Ritchey .................. | G16H 40/63 |
| | | | 348/36 |
| 2013/0095459 A1 * | 4/2013 | Tran ..................... | A61B 5/6816 |
| | | | 434/247 |
| 2014/0156698 A1 * | 6/2014 | Stivoric ............. | G06Q 30/0242 |
| | | | 707/769 |
| 2014/0379273 A1 * | 12/2014 | Petisce .................... | G06F 19/00 |
| | | | 702/19 |
| 2015/0025917 A1 | 1/2015 | Stempora | |
| 2015/0118658 A1 | 4/2015 | Mayou et al. | |
| 2015/0124566 A1 * | 5/2015 | Lake ...................... | G04G 21/08 |
| | | | 368/10 |
| 2015/0223705 A1 * | 8/2015 | Sadhu .................... | G01S 19/17 |
| | | | 600/301 |
| 2015/0273698 A1 | 10/2015 | Bender | |
| 2015/0302301 A1 * | 10/2015 | Petersen .................. | G06N 5/04 |
| | | | 706/11 |
| 2016/0028264 A1 * | 1/2016 | Bernhard ................ | H02J 7/345 |
| | | | 307/21 |
| 2016/0081575 A1 * | 3/2016 | Wu ........................ | G16H 50/30 |
| | | | 600/301 |
| 2016/0174840 A1 | 6/2016 | Udoh et al. | |
| 2016/0293042 A1 | 10/2016 | Pradeep et al. | |
| 2017/0049374 A1 * | 2/2017 | Eldardiry ............... | A61B 5/165 |
| 2017/0071545 A1 * | 3/2017 | Ritscher ............. | A61B 5/02405 |
| 2017/0111722 A1 * | 4/2017 | Forstner ................ | H04R 1/028 |
| 2017/0193711 A1 | 7/2017 | Lenchner | |
| 2018/0067639 A1 * | 3/2018 | Balaram ............. | G06F 3/04883 |
| 2018/0068080 A1 * | 3/2018 | Parate ................. | G06F 19/3418 |
| 2018/0070839 A1 * | 3/2018 | Ritscher ............. | A61B 5/02416 |
| 2018/0122509 A1 * | 5/2018 | Christiansson ........ | G16H 40/63 |
| 2018/0322253 A1 | 11/2018 | Goyal | |
| 2019/0061772 A1 * | 2/2019 | Prinz ........................ | A61B 5/18 |
| 2019/0082987 A1 * | 3/2019 | Varpula ................ | A61B 5/6831 |

OTHER PUBLICATIONS

Smilables, Inc.; Smilables' Baby Brain Development System to Aid New Parents Draws on Scientific Expertise From Top Universities; http://www.prnewswire.com/news/smilables-inc; Jul. 29, 2015; 5 pages.

Sproutling; Sproutling Baby Monitor; http://sproutling.com/; retrieved from the Internet Dec. 9, 2016; 3 pages.

Friedman, Mark J.; List of IBM Patents or Patent Applications Treated as Related; Dec. 8, 2017; 1 page.

* cited by examiner

SENSOR BASED MONITORING

This application is a continuation application claiming priority to Ser. No. 15/587,505 filed May 5, 2017.

FIELD

The present invention relates generally to a method for monitoring conditions of a user and in particular to a method for improving software feedback based monitoring technology associated with enabling sensors for monitoring user conditions and executing associated actions for automatically modifying hardware and software systems associated with modifying the user conditions.

BACKGROUND

Accurately determining user issues typically includes an inaccurate process with little flexibility. Controlling devices associated with correcting the user issues may include a complicated process that may be time consuming and require a large amount of resources. Accordingly, there exists a need in the art to overcome at least some of the deficiencies and limitations described herein above.

SUMMARY

A first aspect of the invention provides a mobile sensor based monitoring improvement method comprising: continuously receiving in real time, by a processor of a controller hardware device via a plurality of sensors integrated within a wearable device of a user, vital sign data and movement based data associated with the user; continuously receiving, by the processor via a plurality of sensors located within a geographical area comprising a current location of the user, environmental data associated with current environmental conditions of the current location of the user; receiving, by the processor from a plurality of remotely located systems, medical data associated with the user; analyzing, by the processor, the vital sign data, the movement based data, the environmental data, and the medical data; predicting, by the processor based on results of the analyzing, current and future mental and physical conditions for the user; generating, by the processor, recommended actions associated with modifying the current and future mental and physical conditions for the user; presenting, by the processor to an authoritative user via a graphical user interface of a hardware device of the authoritative user, the recommended actions; monitoring, by the processor via the plurality of sensors integrated within the wearable device, current physical conditions for the user to determine if the recommended actions have been executed; and transmitting, by the processor to external systems, results of the monitoring.

The present invention advantageously provides a simple method capable of accurately determining user issues.

DETAILED DESCRIPTION

Figure 1:
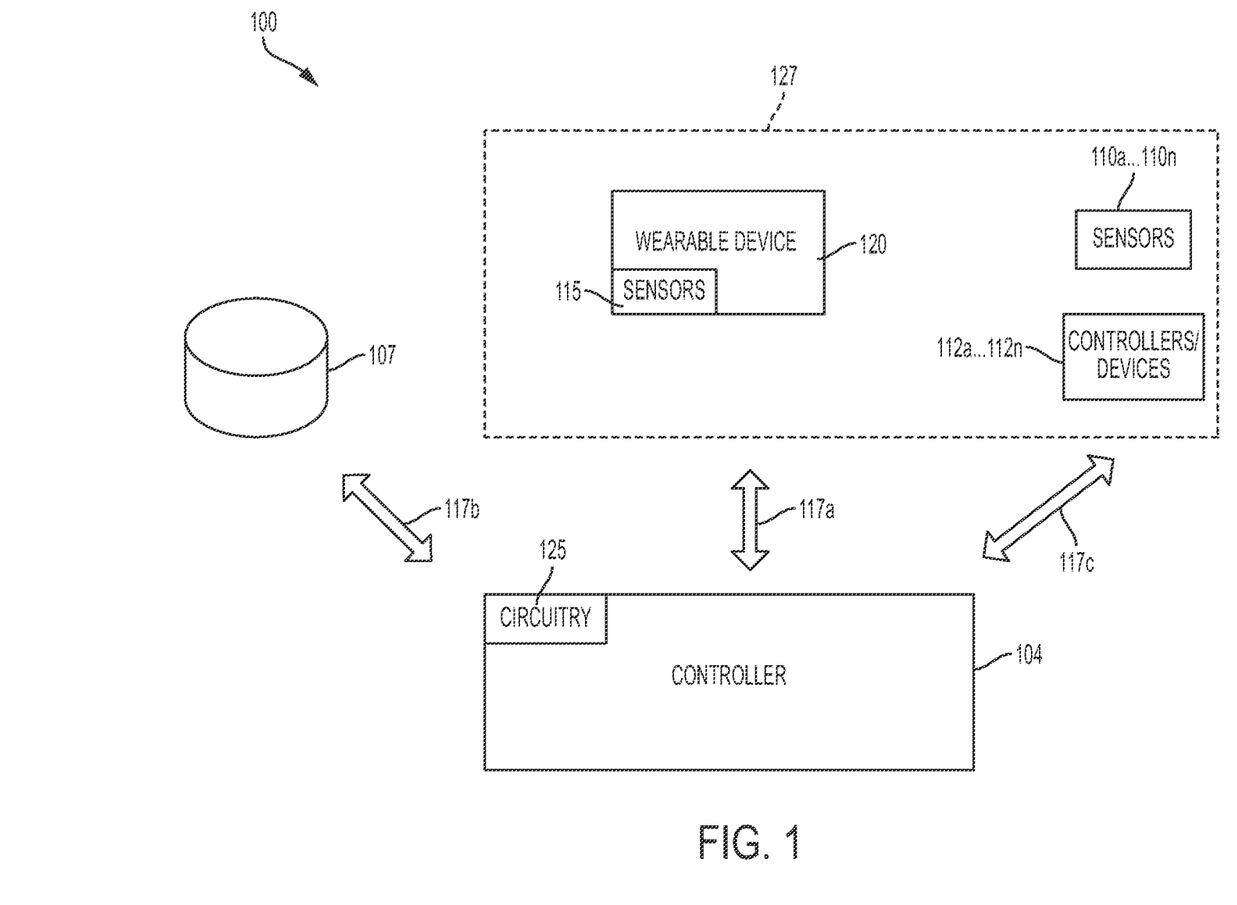
FIG. 1 illustrates a system for improving software feedback based monitoring technology associated with enabling sensors for monitoring user conditions and executing associated actions for automatically modifying hardware and software systems, in accordance with embodiments of the present invention.

FIG. 1 illustrates a system 100 for improving software feedback based monitoring technology associated with enabling sensors for monitoring user conditions and executing associated actions for automatically modifying hardware and software systems, in accordance with embodiments of the present invention. System 100 enables a process for promoting mental and physical growth of a user (e.g., an child) via execution of cognitive hardware and software (e.g., controller 104 and wearable device 120) such as, inter alia, Watson software, artificial intelligence hardware/software, etc. The cognitive hardware and software developed and trained with respect to a large corpus of medical and child rearing data. The aforementioned process includes: (A) continuously receiving (via the cognitive hardware and software) health related data of a user (e.g., vital signs, movement information, etc.) from a sensors of a wearable device attached to the user; (B) predicting current and future mental and physical statuses for the user based on current and historical health data analyzed via the hardware and software; (C) recommending actions for execution with respect to the user (e.g., applying touch, rolling the user over, allowing the user to sleep, etc.); (D) providing the action recommendations to an associated user (e.g., a parent of the user) via a device or software such as a mobile device application (e.g., a health application); and (E) tracking to determine if the recommended actions have been executed. Additionally, impacts of the recommended actions are determined. The device or software may be enabled to allow the associated user to set goals (e.g., gain weight, sleep less, etc.) and track goal progress for the user. The selected goals may be enabled to affect the recommended actions.

System 100 of FIG. 1 includes a controller 104 (i.e., specialized hardware device(s)), a wearable device 120, sensors 110a . . . 110n, controllers/devices 112a . . . 112n, and a database system 120 interconnected through a network 117a, 117b, and 117c. Controller 104 includes specialized circuitry 125 that may include specialized software. Wearable device 120, sensors 110a . . . 110n, and controllers/devices 112a . . . 112n may be located within a specified geographical location/structure 127 (e.g., a building, a room, etc.). Additionally, controller 104 may be located internal or external to geographical location/structure 127. Wearable device 120 comprises internal or integrated sensors 115. Wearable device 120 may comprise any type of wearable device (or a close proximity device) or computer including, inter alia, a smart watch, an activity tracker, jewelry, smart phone, etc. Sensors 115 may include any type of internal or external biomedical sensors including, inter alia, a heart rate monitor, a blood pressure monitor, a thermometer, a pulse rate monitor, an ultrasonic sensor, etc. Sensors 110a ... 110n may include any type of sensors including, inter alia, temperature sensors, humidity sensors, optical sensors, etc. Controllers/devices 112a ... 112n may comprise devices for automatically modifying conditions of specified geographical location/structure 127. For example, controllers/devices 112a ... 112n may comprise automated HVAC systems and automated controllers for modifying a temperature or humidity level of specified geographical location/structure 127. Alternatively, controllers/devices 112a ... 112n may comprise automated medical devices and associated automated controllers for automatically modifying biomedical attributes of the user. Controller 104, wearable device 120, controllers/devices 112a ... 112n, and database system 120 may include specialized testing circuitry/logic. Controller 104, wearable device 120, controllers/devices 112a ... 112n, and database system 120 may each may comprise an embedded device. An embedded device is defined herein as a dedicated device or computer comprising a combination of computer hardware and software (fixed in capability or programmable) specifically designed for executing a specialized function. Programmable embedded computers or devices may comprise specialized programming interfaces. In one embodiment, controller 104, wearable device 120, controllers/devices 112a ... 112n, and database system 120 may each comprise a specialized hardware device comprising specialized (non-generic) hardware and circuitry (i.e., specialized discrete non-generic analog, digital, and logic based circuitry) for (independently or in combination) executing a process described with respect to FIGS. 1-5. The specialized discrete non-generic analog, digital, and logic based circuitry may include proprietary specially designed components (e.g., a specialized integrated circuit, such as for example an Application Specific Integrated Circuit (ASIC) designed for only implementing an automated process for improving software feedback based monitoring technology associated with enabling sensors for monitoring user conditions and executing associated actions for automatically modifying hardware and software systems. Network 117a, 117b, and 117c may include any type of network including, inter alia, a local area network, (LAN), a wide area network (WAN), the Internet, a wireless network, etc. Alternatively, network 117a, 117b, and 117c may include application programming interfaces (API).

System 100 enables a process for generating real time actionable recommendations to authoritative users (e.g., parents and medical professionals) based on current and relevant historical information for a user's (e.g., a patient, a child, etc.) emotional and physical development. System 100 is enabled to generate actionable assessments of user (e.g., a child) development based on current research, individual user history, and currently monitored medical conditions. Executed actions associated with the actionable assessments may be recorded and stored in database 107. The following implementation example describes a process for generating real time actionable recommendations Wearable device 120 may comprise a sensor strap worn by the user (e.g., a patient) for measuring vital signs and moments of the user. A software interface application on controller 104 may record the measurements (from the sensor strap), deliver associated information, and receive alerts based on the measurements from the sensor strap and analyzed data from controller 104. Controller 104 may be enabled to automatically charge the sensor strap and sense environmental conditions, noise levels, and in room disturbances of geographical location/structure 127. Additionally, controller 104 may be comprised by or associated with a cloud server enabled to collect, ingest, and analyze historical and current data from medical records, studies, and journals. The historical and current data may be combined with current user data to determine the associated corrective actions to transmit to the software application. The cloud server may be additionally enabled to record the recommended actions taken and determine the impact of the actions with respect to future outcomes.

The following implementation steps describe a process for improving software feedback based monitoring technology associated with enabling sensors for monitoring user conditions and executing associated actions:

1. A patient wears a sensor strap component such that it is in constant contact with the skin of the patient. The sensor strap records vital sign readings, physical attributes, measurements, and movements of the patient. The recorded information is transmitted to a cloud server component for analysis.
2. A controller component captures environmental data (e.g., conditions in a structure) and recorded information of the sensor strap data for database storage.
3. The cloud server component collects and analyzes all retrieved data and based on the analyzed data, recommended actions are generated and transmitted to a mobile software application for usage by doctors and parents of the patient. Upon execution of the recommended actions, the patient is monitored for physic and mental changes. Over time, system 100 learns which actions care givers are most likely to accept and recommends the actions associated with a highest projected impact that will be accepted by individual patient care givers.

Figure 2:
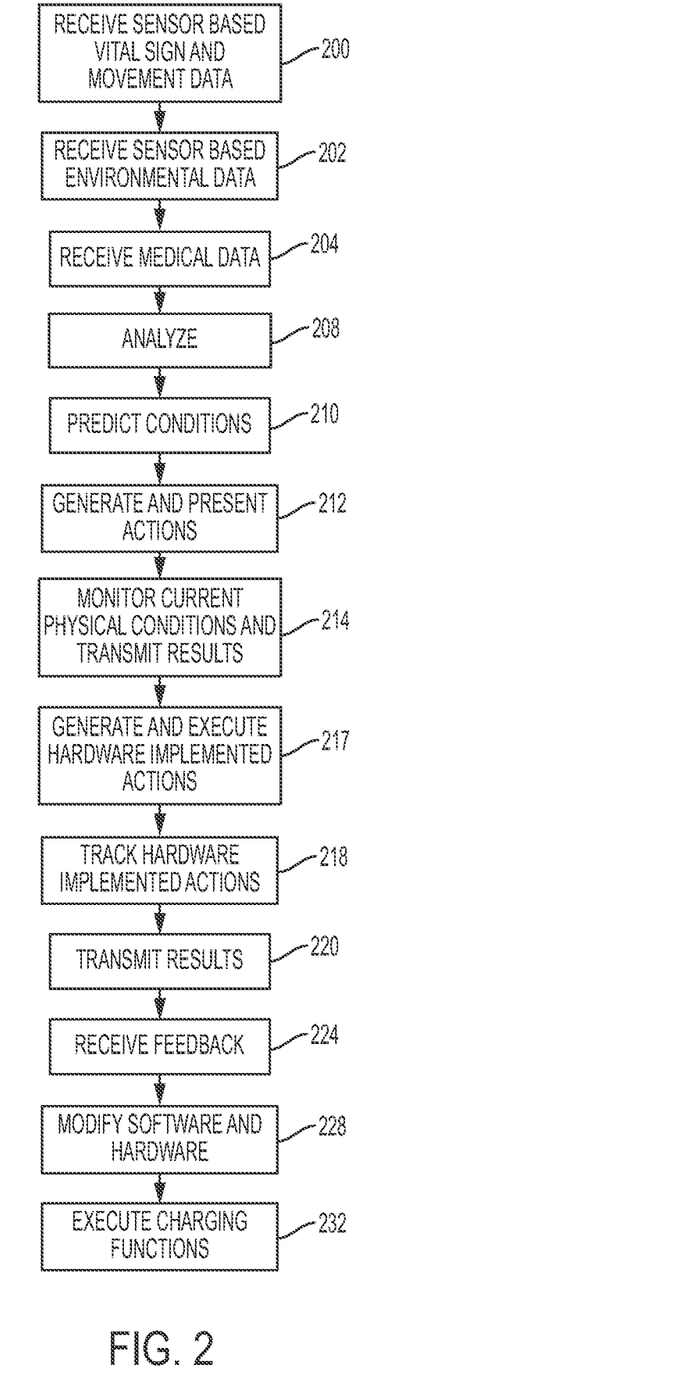
FIG. 2 illustrates an algorithm detailing a process flow enabled by the system of FIG. 1 for improving software feedback based monitoring technology associated with enabling sensors for monitoring user conditions and executing associated actions for automatically modifying hardware and software systems, in accordance with embodiments of the present invention.

FIG. 2 illustrates an algorithm detailing a process flow enabled by system 100 of FIG. 1 for improving software feedback based monitoring technology associated with enabling sensors for monitoring user conditions and executing associated actions for automatically modifying hardware and software systems, in accordance with embodiments of the present invention. Each of the steps in the algorithm of FIG. 2 may be enabled and executed in any order by a computer processor(s) executing computer code. Additionally, each of the steps in the algorithm of FIG. 2 may be enabled and executed in combination by controller 104 and wearable device 120 of FIG. 1. In step 200, vital sign data and movement based data associated with a user is received (continuously receiving in real time by controller hardware device) via a plurality of bio-sensors (e.g., heart rate sensors, temperature sensors, blood pressure sensors, brainwave activity sensors, etc.) integrated within a wearable device of the user. In step 202, environmental data associated with current environmental conditions (e.g., a temperature, a humidity level, a noise level, a lighting level, etc.) of a current location of the user is continuously receiving via a plurality of condition sensors (e.g., temperature sensors, optical sensors, noise sensors, humidity level sensors, etc.) located within a geographical area comprising the current location of the user. In step 204, medical data associated with the user receiving from remotely located systems. In step 208, the vital sign data, the movement based data, the environmental data, and the medical data are analyzed. In step 210, current and future mental and physical conditions for the user are predicted based on results of the analyses of step 208. In step 212, recommended actions associated with modifying the current and future mental and physical conditions for the user are generated and presented to an authoritative user via a graphical user interface of a hardware device of the authoritative user. In step 214, current physical conditions for the user are monitored the plurality of bio-sensors to determine if the recommended actions have been executed. Data associated with the monitoring of step 214 is transmitted to the external systems. In step 217, hardware based actions associated with modifying the current and future mental and physical conditions for the user are generated and executed resulting in a modification of hardware enabled systems associated with the current environmental conditions. Executing the hardware based actions may include automatically modifying HVAC systems associated with the current location of the user thereby modifying the current environmental conditions. Alternatively or additionally, executing the hardware based actions may include automatically modifying medical devices (e.g., a heart rate control device, an oxygen device, etc.) associated with the user thereby modifying biomedical attributes of the user. In step 218, the hardware based actions are tracked (via the plurality of bio-sensors integrated within the wearable device and the plurality of condition sensors located within the geographical area) to determine modifications of the hardware enabled systems. In step 220, results of step 218 are transmitted to the external systems. In step 224, feedback data (associated with the results of step 218) is received from the external systems. In step 228, cognitive software code of the controller hardware device is modified based on said results of step 218. The cognitive software code is enabled for executing future actions resulting in an additional modification of the hardware enabled systems associated with the additional environmental conditions. Alternatively or additionally in step 228, cognitive software code of the controller hardware device may be modified based on said results of step 218. The cognitive software code is enabled for controlling future actions resulting in an additional modification of the hardware enabled systems associated with the additional environmental conditions. In step 232, a voltage level of a power source for the wearable device is detected (via a charge detection circuit of the wearable device) as being less than a predetermined threshold voltage. In response, a charging process for automatically charging the power source is automatically executed. The charging process may comprise a wireless charging process for automatically charging the power source via a wireless charging signal form the controller hardware device.

Figure 3:
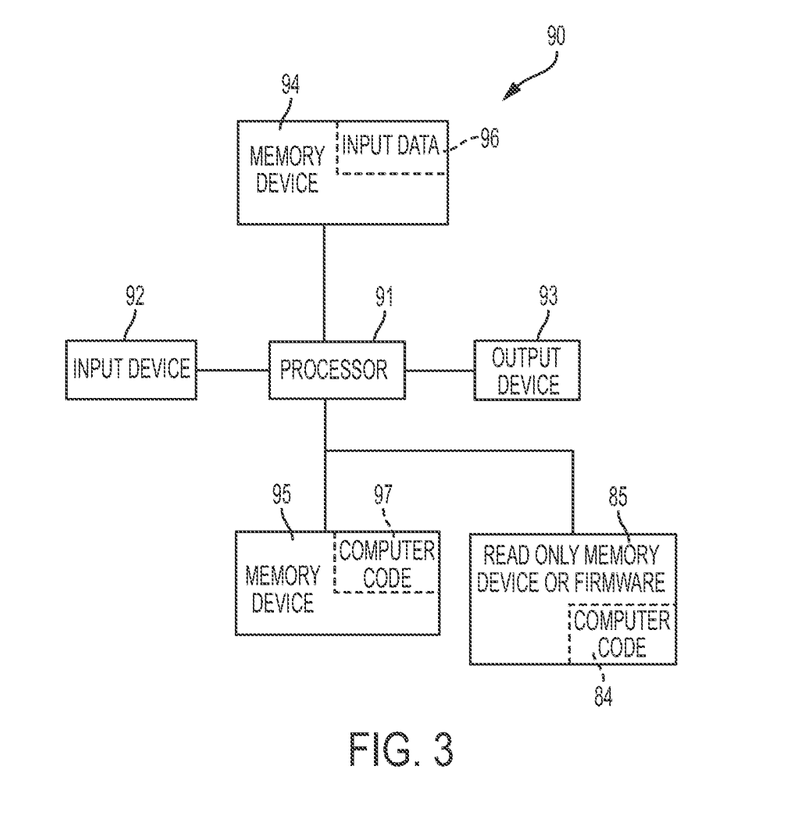
FIG. 3 illustrates a computer system used by the system of FIG. 1 for improving software feedback based monitoring technology associated with enabling sensors for monitoring user conditions and executing associated actions for automatically modifying hardware and software systems, in accordance with embodiments of the present invention.

FIG. 3 illustrates a computer system 90 (e.g., controller 104 and/or wearable device 120 of FIG. 1) used by or comprised by the system of FIG. 1 for improving software feedback based monitoring technology associated with enabling sensors for monitoring user conditions and executing associated actions for automatically modifying hardware and software systems, in accordance with embodiments of the present invention.

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module," or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing apparatus receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, device (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing device to produce a machine, such that the instructions, which execute via the processor of the computer or other programmable data processing device, create means for implementing the functions/acts specified in the flowchart and/or block diagram block or blocks. These computer readable program instructions may also be stored in a computer readable storage medium that can direct a computer, a programmable data processing device, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing device, or other device to cause a series of operational steps to be performed on the computer, other programmable device or other device to produce a computer implemented process, such that the instructions which execute on the computer, other programmable device, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The computer system 90 illustrated in FIG. 3 includes a processor 91, an input device 92 coupled to the processor 91, an output device 93 coupled to the processor 91, and memory devices 94 and 95 each coupled to the processor 91. The input device 92 may be, inter alia, a keyboard, a mouse, a camera, a touchscreen, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes algorithms (e.g., the algorithm of FIG. 2) for improving software feedback based monitoring technology associated with enabling sensors for monitoring user conditions and executing associated actions for automatically modifying hardware and software systems. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices Such as read only memory device 96) may include algorithms (e.g., the algorithm of FIG. 2) and may be used as a computer usable medium (or a computer readable medium or a program storage device) having a computer readable program code embodied therein and/or having other data stored therein, wherein the computer readable program code includes the computer code 97. Generally, a computer program product (or, alternatively, an article of manufacture) of the computer system 90 may include the computer usable medium (or the program storage device).

In some embodiments, rather than being stored and accessed from a hard drive, optical disc or other writeable, rewriteable, or removable hardware memory device 95, stored computer program code 84 (e.g., including algorithms) may be stored on a static, nonremovable, read-only storage medium such as a Read-Only Memory (ROM) device 85, or may be accessed by processor 91 directly from such a static, nonremovable, read-only medium 85. Similarly, in some embodiments, stored computer program code 97 may be stored as computer-readable firmware 85, or may be accessed by processor 91 directly from such firmware 85, rather than from a more dynamic or removable hardware data-storage device 95, such as a hard drive or optical disc.

Still yet, any of the components of the present invention could be created, integrated, hosted, maintained, deployed, managed, serviced, etc. by a service supplier who offers to improve software feedback based monitoring technology associated with enabling sensors for monitoring user conditions and executing associated actions for automatically modifying hardware and software systems. Thus, the present invention discloses a process for deploying, creating, integrating, hosting, maintaining, and/or integrating computing infrastructure, including integrating computer-readable code into the computer system 90, wherein the code in combination with the computer system 90 is capable of performing a method for enabling a process for improving software feedback based monitoring technology associated with enabling sensors for monitoring user conditions and executing associated actions for automatically modifying hardware and software systems. In another embodiment, the invention provides a business method that performs the process steps of the invention on a subscription, advertising, and/or fee basis. That is, a service supplier, such as a Solution Integrator, could offer to enable a process for improving software feedback based monitoring technology associated with enabling sensors for monitoring user conditions and executing associated actions for automatically modifying hardware and software systems. In this case, the service supplier can create, maintain, support, etc. a computer infrastructure that performs the process steps of the invention for one or more customers. In return, the service supplier can receive payment from the customer(s) under a subscription and/or fee agreement and/or the service supplier can receive payment from the sale of advertising content to one or more third parties.

While FIG. 3 shows the computer system 90 as a particular configuration of hardware and software, any configuration of hardware and software, as would be known to a person of ordinary skill in the art, may be utilized for the purposes stated supra in conjunction with the particular computer system 90 of FIG. 3. For example, the memory devices 94 and 95 may be portions of a single memory device rather than separate memory devices.

Cloud Computing Environment

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
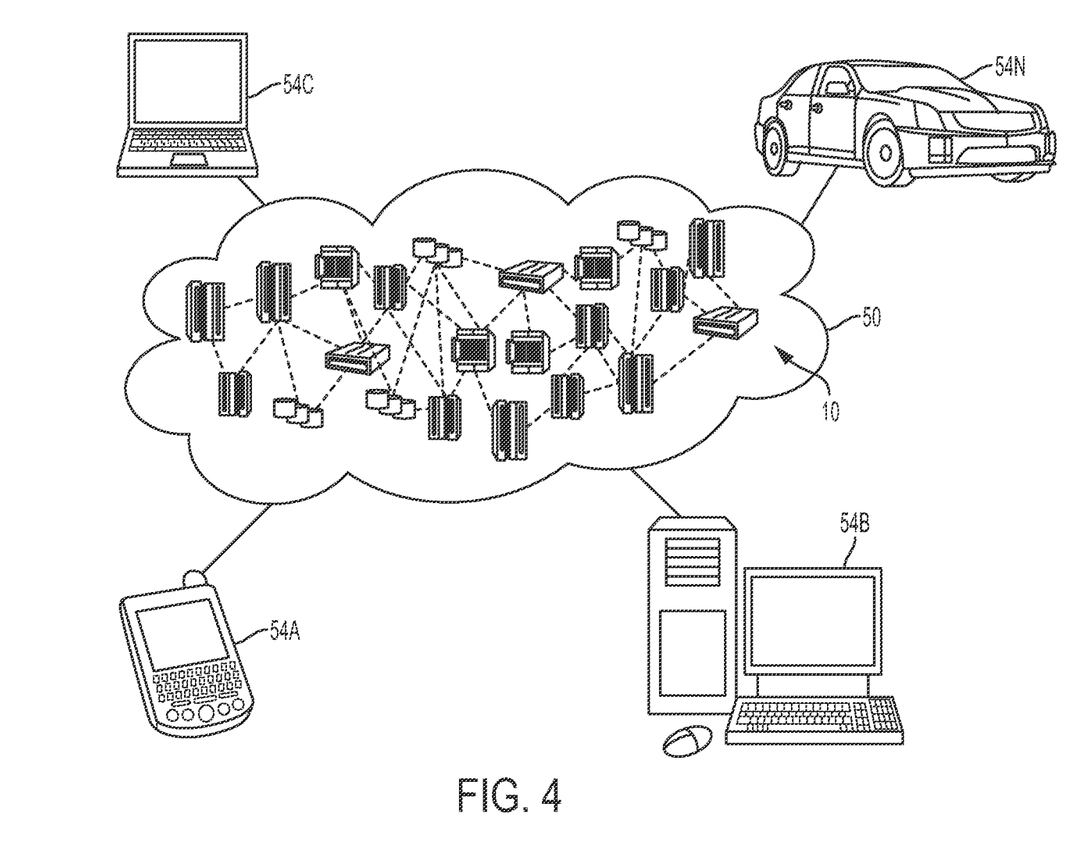
FIG. 4 illustrates a cloud computing environment, in accordance with embodiments of the present invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A, 54B, 54C and 54N shown in FIG. 4 are intended to be illustrative only and that computing nodes 10 and cloud computing environment 50 can communicate with any type of computerized device over any type of network and/or network addressable connection (e.g., using a web browser).

Figure 5:
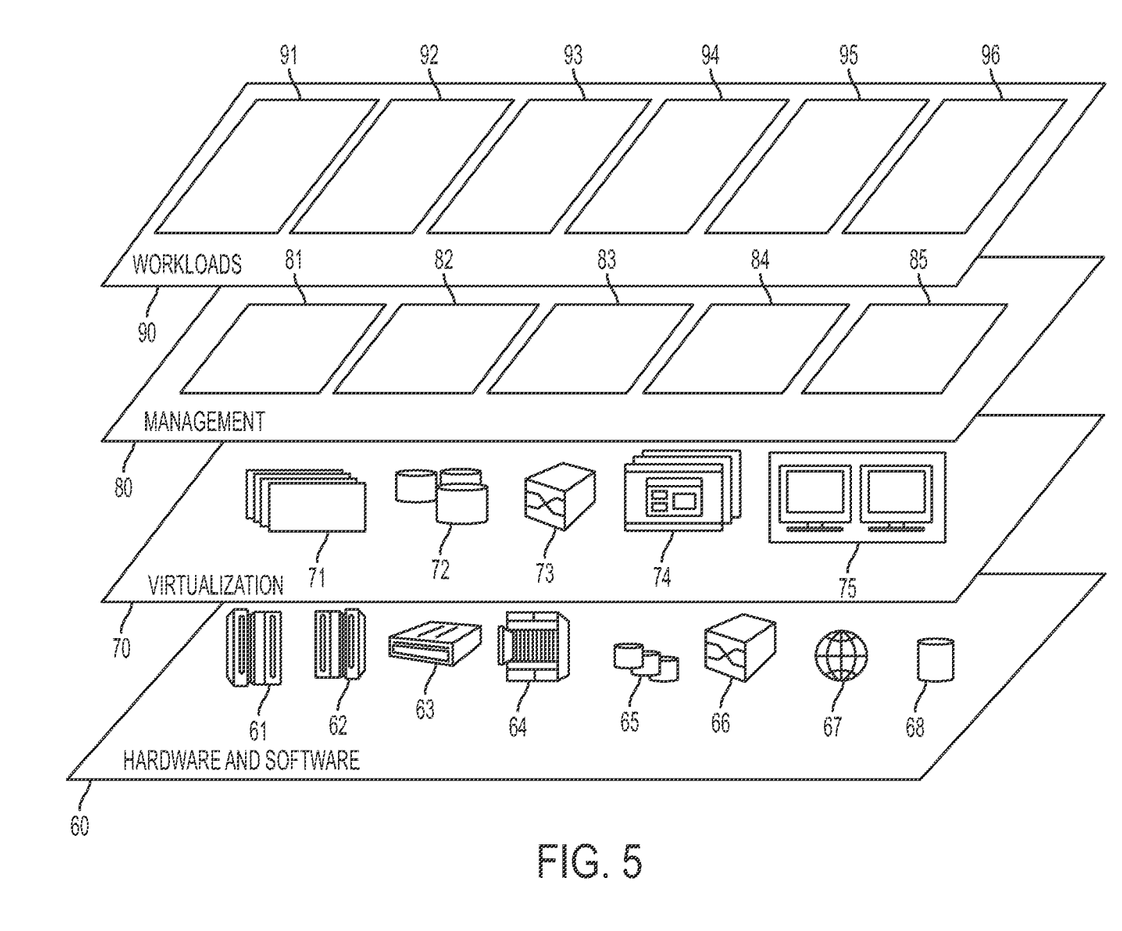
FIG. 5 illustrates a set of functional abstraction layers provided by cloud computing environment, in accordance with embodiments of the present invention.

Referring now to FIG. 5, a set of functional abstraction layers provided by cloud computing environment 50 (see FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 89 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and for improving software feedback based monitoring technology associated with enabling sensors for monitoring user conditions and executing associated actions for automatically modifying hardware and software systems 96.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A mobile sensor based monitoring improvement method comprising:
   continuously receiving in real time, by a processor of a controller hardware device via a plurality of sensors integrated within a sensor strap of a wearable device of a user, vital sign data, physical attribute data, and movement based data associated with said user, wherein said sensor strap is in constant contact with the skin of said user;
   continuously receiving, by said processor via a plurality of sensors located within a geographical area comprising a current location of said user, environmental data associated with current environmental conditions and in room disturbances within a structure of said current location of said user, wherein said current environmental conditions comprise a noise level at said current location;
   receiving, by said processor from a plurality of remotely located systems, medical data associated with said user;
   analyzing, by said processor via execution of artificial intelligence hardware and software, said vital sign data, said physical attribute data and, said movement based data, said environmental data, and said medical data;
   predicting, by said processor based on results of said analyzing, current and future mental and physical conditions for said user;
   generating, by said processor, recommended actions associated with modifying said current and future mental and physical conditions for said user;
   presenting, by said processor to an authoritative user via a graphical user interface of a hardware device of said authoritative user, said recommended actions;
   executing, by said processor, said recommended actions such that said user is physically moved in accordance with said current and future mental and physical conditions for said user;
   sensor based monitoring, by said processor via said plurality of sensors integrated within said wearable device, current physical conditions and associated physical and mental condition changes with respect to previous physical and mental condition changes for said user to auto-determine if said recommended actions and user condition based actions have been executed;
   transmitting, by said processor to external systems, results of said monitoring;
   detecting, by said processor via a charge detection circuit of said wearable device, that a voltage level of a power source for said wearable device is less than a predetermined threshold voltage;
   executing, by said processor via a charging circuit of said wearable device, a charging process comprising automatically charging, from a controller hardware device via a wireless charging signal applied to said power source and said sensor strap from said controller hardware device, said power source and said sensor strap;
   generating, by said processor, hardware based actions associated with modifying said current and future mental and physical conditions for said user;
   executing, by said processor, said hardware based actions resulting in a modification of hardware enabled systems associated with said current environmental conditions; wherein said executing said hardware based actions comprises modifying a heart rate control device and an oxygen device of said user thereby modifying a heart-rate and an oxygen level of said user; and
   modifying, by said processor based on said results of said executing, cognitive software code of said wearable device for controlling future actions resulting in an additional modification of said hardware enabled systems associated with additional environmental conditions.

2. The method of claim 1, wherein said executing said hardware based actions further comprises automatically modifying HVAC systems associated with said current location of said user thereby modifying said current environmental conditions.

3. The method of claim 1, wherein said executing said hardware based actions further comprises automatically modifying medical devices associated with said user thereby modifying biomedical attributes of said user.

4. The method of claim 1, further comprising:
   tracking, by said processor via said plurality of sensors integrated within said wearable device and said plurality of sensors located within said geographical area, said hardware based actions to determine said modification of said hardware enabled systems; and transmitting, by said processor to said external systems, results of said tracking.

5. The method of claim 4, further comprising:
receiving, by said processor based on said results of said tracking, input data from said external systems; and
modifying, by said processor based on said results of said tracking and said input data, cognitive software code of said controller hardware device for executing future actions resulting in an additional modification of said hardware enabled systems associated with additional environmental conditions.

6. The method of claim 4, further comprising:
receiving, by said processor based on said results of said tracking, input data from said external systems.

7. The method of claim 1, wherein said current environmental conditions comprise a temperature of said current location and a humidity level of said current location.

8. The method of claim 1, wherein said current environmental conditions comprise a noise level at said current location and a lighting level at said current location, and wherein said executing said actions comprises automatically modifying said noise level and said lighting level.

9. The method of claim 1, wherein said plurality of sensors integrated within said wearable device comprise heart rate sensors, temperature sensors, blood pressure sensors, and brainwave activity sensors.

10. The method of claim 1, wherein said plurality of sensors located within said geographical area comprise temperature sensors, optical sensors, noise sensors, and humidity level sensors.

11. The method of claim 1, further comprising:
providing at least one support service for at least one of creating, integrating, hosting, maintaining, and deploying computer-readable code in the control hardware, said code being executed by the computer processor to implement: said continuously receiving in real time, said continuously receiving said environmental data, said receiving, said analyzing, said predicting, said generating, said presenting, said monitoring, and said transmitting.

* * * * *